(12) United States Patent
Kim et al.

(10) Patent No.: US 9,006,349 B2
(45) Date of Patent: Apr. 14, 2015

(54) TEMPERATURE-SENSITIVE POLYETHYLENE GLYCOL / POLYESTER BLOCK COPOLYMER IN WHICH BIOACTIVE FUNCTIONAL GROUP IS INTRODUCED INTO SIDE CHAIN THEREOF

(75) Inventors: Moon Suk Kim, Yongin-si (KR); Jae Il Kim, Suwon-si (KR)

(73) Assignee: Ajou University Industry-Academic Cooperation Foundation, Suwon-Si, Gyeonggi-Do (KR)

(*) Notice: Subject to any disclaimer, the term of this patent is extended or adjusted under 35 U.S.C. 154(b) by 0 days.

(21) Appl. No.: 13/983,905

(22) PCT Filed: Nov. 22, 2011

(86) PCT No.: PCT/KR2011/008931
§ 371 (c)(1),
(2), (4) Date: Aug. 6, 2013

(87) PCT Pub. No.: WO2012/108614
PCT Pub. Date: Aug. 16, 2012

(65) Prior Publication Data
US 2013/0331526 A1 Dec. 12, 2013

(30) Foreign Application Priority Data
Feb. 8, 2011 (KR) .................. 10-2011-0011278

(51) Int. Cl.
*A61K 47/34* (2006.01)
*C08L 71/02* (2006.01)
*C08L 67/04* (2006.01)
*A61K 47/48* (2006.01)
*C08G 63/664* (2006.01)
*C08G 63/91* (2006.01)
*A61K 9/00* (2006.01)
*A61L 31/06* (2006.01)
*A61L 31/14* (2006.01)
*A61L 31/16* (2006.01)

(52) U.S. Cl.
CPC .............. *A61K 47/34* (2013.01); *A61K 47/482* (2013.01); *A61K 47/48215* (2013.01); *C08G 63/664* (2013.01); *C08G 63/912* (2013.01); *C08L 71/02* (2013.01); *C08G 2261/126* (2013.01); *C08L 2205/05* (2013.01); *A61K 9/0024* (2013.01); *A61L 31/06* (2013.01); *A61L 31/14* (2013.01); *A61L 31/145* (2013.01); *A61L 31/16* (2013.01)

(58) Field of Classification Search
CPC .............. A61K 47/34; A61K 47/482; A61K 47/48215; C08L 71/02; C08L 2205/05; C08G 63/08; C08G 63/664; C08G 63/912; C08G 2261/126
USPC ............ 528/271, 354; 252/415, 437, 440.08, 252/443
See application file for complete search history.

(56) References Cited

U.S. PATENT DOCUMENTS

2008/0107704 A1* 5/2008 Guo .............................. 424/423

FOREIGN PATENT DOCUMENTS

| KR | 100668046 | 1/2007 |
| KR | 1020080075387 | 8/2008 |
| KR | 1020090059880 | 6/2009 |
| KR | 1020100097144 | 9/2010 |

OTHER PUBLICATIONS

Noga et al. (Synthesis and Modification of Functional Poly(lactide) Copolymers: Toward Biofunctional Materials, Biomacromolecules 2008, 9, 2056-2062).*
Definition of Room Temperature from Hawley's Chemical Dictionary.*
Tang (Controlled Delivery of Therapeutic Agents from Poylmer-basd, in Situ, Gel Forming Systems, 2008 p. 62).*
Gerhardt et al (Functionalized Lactide Monomers: Methodology and Polymerization, Biomacromolecules, 7, pp. 1735-1742 Jun. 2006).*
Hyun et al (Preparation of Diblock Copolymers Consisting of Methoxy Polyethylene Glycol and Poly e-caprolactone/poly l-lactide and their degradation property, Polymer Engineering and Science, 46, 9, pp. 1242-1249, Sep. 2006).*
Moon Suk Kim et al., Preparation of Thermosensitive Diblock Copolymers Consisting of MPEG and Polyesters, May 2, 2006, 4 pages, vol. 39, No. 9, American Chemical Society, Jeonju, Korea.
Yan Liu et al., New Biodegradable Polymers from Renewable Sources: Polyester-carbonates Based on 1,3-Propylene-co-1, 4-Cyclohexanedimethylene Succinate, Journal of Polymer Science, 12 pages, vol. 39, John Wiley&Sons, Inc.
Masahiko Okada et al., Biodegradable Polymers Based on Renewable Resources. V. Synthesis and Biodegradation Behavior of Poly(esteramide)s Composed of 1,4:3,6-Dianhydro-D-glucitol, a-Amino Acid, and Aliphatic Dicarboxylic Acid Units, Journal of Applied Polymer Science, 14 pages, vol. 81, Jon Wiley &Sons, Inc.
International Search Report mailed May 23, 2012 for PCT/KR2011/008931, citing the above reference(s).
International Preliminary Report for international application No. PCT/KR2011/008931 dated Aug. 22, 2013.
Written Opinion of the International Searching Authority for international application No. PCT/KR2011/008931 dated May 23, 2012.

* cited by examiner

*Primary Examiner* — Randy Gulakowski
*Assistant Examiner* — Christopher M Rodd
(74) *Attorney, Agent, or Firm* — Lowe Hauptman & Ham, LLP (57) ABSTRACT

The present invention relates to preparation and application of a temperature-sensitive polyethylene glycol/polyester block copolymer having a bioactive functional group introduced into a side chain thereof. More specifically, it relates to a temperature-sensitive polyethylene glycol/polyester block copolymer including a lactide segment having a bioactive functional group introduced into a side chain thereof and a method for preparing same. The temperature-sensitive polyethylene glycol/polyester block copolymer according to the present invention having a bioactive functional group introduced into a side chain thereof can be widely used as a drug delivery system, a support for tissue engineering, an adhesion inhibitor, etc.

10 Claims, 8 Drawing Sheets

| | Carbon (mol%) | Hydrogen (mol%) | Nitrogen (mol%) | N/C |
|---|---|---|---|---|
| Example 5 | 58.22 | 8.40 | 1.21 | 0.021 |

TEMPERATURE-SENSITIVE POLYETHYLENE GLYCOL / POLYESTER BLOCK COPOLYMER IN WHICH BIOACTIVE FUNCTIONAL GROUP IS INTRODUCED INTO SIDE CHAIN THEREOF

CROSS-REFERENCE TO RELATED APPLICATIONS

This application claims priority under 35 U.S.C. §119 to Korean Patent Application No. 10-2011-0011278, filed on Feb. 8, 2011, in the Korean Intellectual Property Office, the disclosure of which is incorporated herein by reference in its entirety.

BACKGROUND (a) Technical Field

The present invention relates to a temperature-sensitive polyethylene glycol/polyester block copolymer having a bioactive functional group introduced into a side chain thereof, more particularly to a temperature-sensitive polyethylene glycol/polyester block copolymer including a lactide segment having a specific bioactive functional group such as a benzyl ether group introduced into a side chain thereof.

(b) Background Art

At present, research has been focused on temperature-sensitive hydrogels for application to drug delivery systems and tissue engineering applications utilizing their change in physical and chemical properties in response to external stimulation. For a temperature-sensitive hydrogel to be utilized for injectable drug delivery systems and tissue engineering applications, it should exhibit low viscosity, fast gelation, biodegradability and low molecular weight to be easily cleared from human body. Further, to be used as a biomaterial, it should be biocompatible and should not damage cells or organs during degradation or clearance from human body.

To solve this problem, block copolymers of a biodegradable and temperature-sensitive polyethylene glycol with a biodegradable ester such as caprolactone, lactide, p-dioxanone and trimethylene carbonate, which exhibit different sol-to-gel phase transition behaviors depending on temperature and concentration, have been studied [M. S. Kim, H. Hyun, G. S. Khang et al, *Macromolecules*, 39, 3099-3102 (2006)].

These studies present biocompatible and biodegradable block copolymers that can be degraded to biological metabolites through dissolution, chemical hydrolysis, etc. and cleared from human body using biodegradable ester-based polymers which are highly soluble in water and organic solvents, nontoxic and immunorejection free and polyethylene glycol which allows control of degradation period of copolymers when introduced through chemical bonding by increasing the amount of water that can be absorbed by the polymers.

Despite these advantages, the conventional temperature-sensitive gels are limited in medical applications because they lack functional groups. In particular, the existing biodegradable polyesters are limited in exhibiting stable drug loading and controlled drug release due to lack functional groups and show side effects such as adsorption to protein surfaces, unwanted modification of drugs, localized accumulation of hydrolysis products, etc.

To introduce functional groups into polyester, copolymerization of cyclic ester compounds with polyethylene glycol, polyvinyl alcohol, heparin, aspartic acid, etc. has been studied [*J. Polym. Sci. Part A: Polym Chem.* 39 (2001), 2508, *J. Appl. Polym. Sci.* 81 (2001), 2721]. Although hydrophobicity can be conferred to polyester through approach, further modification is limited because of limitation of the functional groups and the possibility that degradation products may result in undesirable side effects cannot be excluded.

SUMMARY

The inventors of the present invention have made efforts to solve the problems of the existing art. As a result, they have found out that the temperature-sensitive behavior of a hydrogel can be controlled by introducing various bioactive functional groups to a lactide segment of a polyethylene glycol/polyester block copolymer and stable drug loading can be achieved by inducing interaction with a drug.

The present invention is directed to providing a temperature-sensitive polyethylene glycol/polyester block copolymer including a lactide segment having various bioactive functional groups such as a benzyl ether group introduced into a side chain thereof.

The present invention is also directed to providing a method for preparing the temperature-sensitive polyethylene glycol/polyester block copolymer.

Finally, the present invention is also directed to providing a drug delivery system, a support for tissue engineering, or an adhesion inhibitor including the polyethylene glycol/polyester block copolymer.

In an aspect, the present invention provides a temperature-sensitive polyethylene glycol/polyester block copolymer including a lactide segment having a bioactive functional group introduced into a side chain thereof.

In another aspect, the present invention provides a temperature-sensitive polyethylene glycol/polyester block copolymer including: a hydrophilic moiety including polyethylene glycol; and a polyester-based hydrophobic moiety of Chemical Formula 1 including a caprolactone segment and a lactide segment having a bioactive functional group R introduced into a side chain thereof:

[Chemical Formula 1]

wherein x and y are mole fractions of the caprolactone segment and the lactide segment having the bioactive functional group R introduced, with x/y being from 0.01/99.99 to 99.99/0.01, and R is —$CH_2$O—$R_1$—$C_6H_5$, —$CH_2$—$R_1$—OH, —$CH_2$O—$R_1$—COOH, —$CH_2$O—$R_1$—$NH_2$, —$CH_2$O—$R_1$—NH—$R_2$, —$CH_2$O—$R_1$—NH—$R_1$—$NH_2$, —$CH_2$O—$R_1$—NH-peptide, Arg-Gly-Asp, Gly-Pro-Glu, Arg-Gly-Asp-Ser, Gly-Gly-Ala, Gly-Arg-Gly-Asp-Ser, Gly-Arg-Gly-Asp-Thr-Pro, Gly-Arg-Gly-Asp-Ser-Pro, a protein including an amine structure or a polyamine having a molecular weight of 350-2,000 g/mole, wherein $R_1$ is ($C_1$-$C_{20}$) alkylene with or without carbonyl, ($C_2$-$C_{20}$) alkenylene with or without carbonyl or ($C_2$-$C_{20}$) alkynylene with or without carbonyl and $R_2$ is ($C_1$-$C_{20}$) alkyl with or without carbonyl, ($C_2$-$C_{20}$) alkenyl with or without carbonyl or ($C_2$-$C_{20}$) alkynyl with or without carbonyl.

In another aspect, the present invention provides a method for preparing a temperature-sensitive polyethylene glycol/polyester block copolymer, including: (a) drying polyethylene glycol through azeotropic distillation; and (b) performing polymerization after adding caprolactone and lactide having a bioactive functional group introduced into a side chain thereof to the polyethylene glycol as monomers.

In another aspect, the present invention provides a drug delivery system, a support for tissue engineering or an adhesion inhibitor including the polyethylene glycol/polyester block copolymer.

Other features and aspects of the present invention will be apparent from the following detailed description, drawings and claims.

BRIEF DESCRIPTION OF THE DRAWINGS

The above and other objects, features and advantages of the present invention will now be described in detail with reference to certain exemplary embodiments thereof illustrated in the accompanying drawings which are given hereinbelow by way of illustration only, and thus are not limitative of the invention, and wherein.

DETAILED DESCRIPTION

Hereinafter, reference will now be made in detail to various embodiments of the present invention, examples of which are illustrated in the accompanying drawings and described below. While the invention will be described in conjunction with exemplary embodiments, it will be understood that the present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The present invention relates to a temperature-sensitive polyethylene glycol/polyester block copolymer including a hydrophilic moiety including polyethylene glycol (PEG) and a hydrophobic moiety including an ester-based caprolactone (CL) segment and a lactide (BMDD) segment having various bioactive functional groups bonded to a side chain thereof. The block copolymer of the present invention has tunable temperature sensitivity since various bioactive functional groups can be introduced into a side chain thereof and may be used for a drug delivery system, a support for tissue engineering or an adhesion inhibitor.

Hereinafter, the present invention is described in further detail.

The present invention relates to a temperature-sensitive polyethylene glycol/polyester block copolymer having a bioactive functional group introduced into a side chain thereof and a method for preparing same. More particularly, the present invention relates to a temperature-sensitive polyethylene glycol/polyester block copolymer including a hydrophilic moiety including polyethylene glycol and a biodegradable polyester-based hydrophobic moiety including a caprolactone (CL) segment and a novel lactide (BMDD) segment having a bioactive functional group introduced into a side chain thereof.

The polyethylene glycol (PEG) used as a polymerization initiator in the polyethylene glycol/polyester block copolymer according to the present invention has many advantages suitable for use in drug delivery and tissue engineering. It can easily load and release a drug, is highly soluble in water and organic solvents, is nontoxic and exhibits excellent biocompatibility with no immunorejection. As such, it is approved for use in human by the US Food and Drug Administration and is used in the pharmaceutical industry. Also, since PEG is a hydrophilic polymer that exhibits the highest inhibitory effect against protein adsorption and improves biocompatibility of materials contacting with blood, it is widely used as a biomaterial.

An ester-based biodegradable polymer is advantageous in that the degradation period can be controlled by controlling molecular weight and chemical composition. The polyethylene glycol (PEG)- and polycaprolactone (PCL)-co-polylactide (PLLA)-based block copolymer used in the present invention is a temperature-sensitive copolymer that exhibits sol-to-gel phase transition property and is already used as a biomaterial in tissue engineering applications and drug delivery systems. Lactide is included in the copolymer to decrease crystallinity and control the biodegradation period. In the present invention, novel lactide monomers having bioactive functional groups are prepared and various functional groups are introduced into the side chain of the copolymer through polymerization to control the biodegradation period and temperature-sensitive behavior of the copolymer.

In the present invention, a molar ratio x/y of the caprolactone segment and the lactide segment having a bioactive functional group at a side chain thereof in the hydrophobic moiety of the copolymer may be from 0.01/99.99 to 99.99/0.01, more specifically from 50/50 to 99/1, most specifically from 70/30 to 99/1, to ensure fast temperature response.

In the present invention, the polyethylene glycol may be one having a molecular weight of 350-2,000 g/mole, specifically 350-1,500 g/mole.

The temperature-sensitive polyethylene glycol/polyester block copolymer according to the present invention may have a molecular weight of 2,000-6,000 g/mole, more specifically 2,000-5,000 g/mole. If the molecular weight of the block copolymer is smaller than 2,000 g/mole, sol-to-gel phase transition may not occur at the human body temperature and the block copolymer may remain in sol phase. And, if the molecular weight exceeds 6,000 g/mole, a lot of time may be necessary for biodegradation of the block copolymer. Hence, the above range is preferred.

The temperature-sensitive polyethylene glycol/polyester block copolymer according to the present invention is in sol phase having flowability at room temperature but is in gel phase at 20-60° C. Above the critical temperature, the block copolymer returns to the sol phase exhibiting flowability.

The present invention also provides temperature-sensitive polyethylene glycol/polyester block copolymers wherein various functional groups are introduced into side chains thereof. The introduction of the functional groups allows control of temperature-sensitive behavior. Accordingly, the block copolymer can be used for an injectable drug delivery system that can easily load and release a drug or a bioactive agent depending on change in temperature.

Specifically, the present invention provides a polyethylene glycol/polyester block copolymer having a functional group introduced, including a hydrophilic moiety including polyethylene glycol and a hydrophobic moiety represented by Chemical Formula 1, the hydrophobic moiety including a caprolactone segment and a lactide segment that are randomly copolymerized.

That is to say, in the hydrophobic moiety represented by Chemical Formula 1, the segments are copolymerized randomly and irregularly and various functional groups may be introduced into a side chain thereof.

[Chemical Formula 1]

In Chemical Formula 1, x and y are mole fractions of the caprolactone segment and the lactide segment having the bioactive functional group R introduced, with x/y being from 0.01/99.99 to 99.99/0.01, and R is —$CH_2$O—$R_1$—$C_6H_5$, —$CH_2$—$R_1$—OH, —$CH_2$O—$R_1$—COOH, —$CH_2$O—$R_1$—$NH_2$, —$CH_2$O—$R_1$—NH—$R_2$, —$CH_2$O—$R_1$—NH—$R_1$—$NH_2$, —$CH_2$O—$R_1$—NH-peptide, Arg-Gly-Asp, Gly-Pro-Glu, Arg-Gly-Asp-Ser, Gly-Gly-Ala, Gly-Arg-Gly-Asp-Ser, Gly-Arg-Gly-Asp-Thr-Pro, Gly-Arg-Gly-Asp-Ser-Pro, a protein comprising an amine structure or a polyamine having a molecular weight of 350-2,000 g/mole, wherein $R_1$ is ($C_1$-$C_{20}$) alkylene with or without carbonyl, ($C_2$-$C_{20}$) alkenylene with or without carbonyl or ($C_2$-$C_{20}$) alkynylene with or without carbonyl and $R_2$ is ($C_1$-$C_{20}$) alkyl with or without carbonyl, ($C_2$-$C_{20}$) alkenyl with or without carbonyl or ($C_2$-$C_{20}$) alkynyl with or without carbonyl.

More specifically, the molar ratio x/y of the caprolactone segment and the lactide segment having the functional group R introduced may be from 70/30 to 99/1 and R may be —$CH_2$O—$CH_2$—$C_6H_5$, —$CH_2$—OH, —$CH_2$O—CO—($CH_2$)$_3$—COOH, —$CH_2$O—($CH_2$)$_3$—COOH, —$CH_2$O—$CH_2$—CH($CH_3$)—$NH_2$, —$CH_2$O—$CH_2$—CO—NH—$CH_2$—$NH_2$, —$CH_2$O—($CH_2$)$_3$—CO—NH-peptide or —$CH_2$O—CO—($CH_2$)$_3$—NH-peptide. The peptide may be a bioactive peptide consisting of 1-50, more specifically 1-10, amino acids. More specifically, the peptide may be selected from Arg-Gly-Asp, Gly-Pro-Glu, Arg-Gly-Asp-Ser, Gly-Gly-Ala, Gly-Arg-Gly-Asp-Ser, Gly-Arg-Gly-Asp-Thr-Pro and Gly-Arg-Gly-Asp-Ser-Pro for better biocompatibility.

The functional group R may have an amine (—$NH_2$) group at the end of the molecular chain for easier introduction of another bioactive functional group.

The present invention also provides a method for preparing a lactide monomer having a benzyl ether group, which is used for preparation of the copolymer described above. The lactide monomer having a benzyl ether group may be prepared according to Scheme 1.

[Scheme 1]

A representative example of synthesis of biocompatible, biodegradable and temperature sensitivity controllable polyethylene glycol/polyester block copolymers having various functional groups is shown in Scheme 2.

ther reacted with, for example, one or more compound selected from a group consisting of succinic anhydride, glutaric anhydride, methylsuccinic anhydride, 2,2-dimethylsuccinic anhydride and 3,3-tetramethyleneglutaric anhydride, a

[Scheme 2]

In Scheme 2, n is an integer representing the number of polyethylene glycol repeat units of the hydrophilic moiety and x and y are mole fractions of the segments of the hydrophobic polyester moiety.

In the present invention, low-molecular-weight ($M_n$=350-2,000 g/mole) polyethylene glycol as a hydrophilic moiety is copolymerized with ester-based caprolactone (CL) and lactide (BMDD) having a benzyl ether group at a side chain by ring-opening copolymerization. After drying the polyethylene glycol through azeotropic distillation, the ester-based caprolactone (CL) and the lactide (BMDD) having a benzyl ether group at the side chain are added as monomers and polymerization is performed at 100-130° C. using an $Sn(Oct)_2$ catalyst as an activator after adding toluene as a reaction solvent. As a result, a temperature-sensitive polyethylene glycol/polyester block copolymer is prepared.

If the benzyl ether group of the temperature-sensitive polyethylene glycol/polyester block copolymer is reduced, a temperature-sensitive polyethylene glycol/polyester block copolymer having a hydroxyl group introduced can be prepared.

If the temperature-sensitive polyethylene glycol/polyester block copolymer having a hydroxyl group introduced is further reacted with, for example, one or more compound selected from a group consisting of succinic anhydride, glutaric anhydride, methylsuccinic anhydride, 2,2-dimethylsuccinic anhydride and 3,3-tetramethyleneglutaric anhydride, a temperature-sensitive polyethylene glycol/polyester block copolymer having a carboxyl group introduced can be prepared. If it is reacted with one or more selected from a group consisting of Arg-Gly-Asp, Gly-Pro-Glu, Arg-Gly-Asp-Ser, Gly-Gly-Ala, Gly-Arg-Gly-Asp-Ser, Gly-Arg-Gly-Asp-Thr-Pro and Gly-Arg-Gly-Asp-Ser-Pro, a temperature-sensitive polyethylene glycol/polyester block copolymer having a peptide introduced can be prepared. If it is reacted with proteins having various amine structures, temperature-sensitive polyethylene glycol/polyester block copolymers having proteins introduced can be prepared. And, if it is reacted with a lower amine or a polyamine having a molecular weight of 350-2,000 g/mole, a temperature-sensitive polyethylene glycol/polyester block copolymer having a polyamine introduced can be prepared. Various functional groups can be introduced in this manner, although not being limited thereto. Also, the above reactions may be performed as a combination of two or more.

Examples of the polyethylene glycol/polyester block copolymers according to the present invention that can be prepared by varying the mole fractions of the segments of the hydrophobic moiety and the bioactive functional groups are summarized in Table 1.

TABLE 1

| polymer | [CL]/[fLA] molar ratio in feed | [CL]/[fLA] molar ratio in polymer[a] | $M_{n\ calcd}$[a] | Yield(%)[b] | $M_w/M_n$[c] |
|---|---|---|---|---|---|
| $MC_{97}L_3$-OBn | 97/3 | 97.2/2.8 | 2390/150 | 87[b1] | 1.28 |
| $MC_{97}L_3$-OH | | | 2390/110 | 92[b2] | 1.30 |
| $MC_{97}L_3$-COOH | | | 2390/110-390 | 68[b3] | 1.30 |
| $MC_{95}L_5$-OBn | 95/5 | 95.7/4.3 | 2340/230 | 89[b1] | 1.31 |
| $MC_{95}L_5$-OH | | | 2340/170 | 92[b2] | 1.30 |
| $MC_{95}L_5$-COOH | | | 2340/170-530 | 70[b3] | 1.31 |
| $MC_{93}L_7$-OBn | 93/7 | 93.5/6.5 | 2100/320 | 85[b1] | 1.36 |
| $MC_{93}L_7$-OH | | | 2100/210 | 82[b2] | 1.36 |
| $MC_{93}L_7$-COOH | | | 2100/210-690 | 69[b3] | 1.37 |
| $MC_{90}L_{10}$-OBn | 90/10 | 91.0/9.0 | 2030/440 | 86[b1] | 1.34 |
| $MC_{90}L_{10}$-OH | | | 2030/280 | 87[b2] | 1.34 |

TABLE 1-continued

| polymer | [CL]/[fLA] molar ratio in feed | [CL]/[fLA] molar ratio in polymer[a] | $M_{n\ calcd}$[a] | Yield(%)[b] | $M_w/M_n$[c] |
|---|---|---|---|---|---|
| $MC_{90}L_{10}$-COOH | | | 2030/280-740 | 66[b3] | 1.36 |
| $MC_{87}L_{13}$-OBn | 87/13 | 87.9/12.1 | 2080/630 | 87[b1] | 1.34 |
| $MC_{87}L_{13}$-OH | | | 2080/400 | 83[b2] | 1.35 |
| $MC_{87}L_{13}$-COOH | | | 2080/400-820 | 70[b3] | 1.35 |
| $MC_{85}L_{15}$-OBn | 85/15 | 85.6/14.4 | 1830/670 | 82[b1] | 1.36 |
| $MC_{85}L_{15}$-OH | | | 1830/430 | 86[b2] | 1.36 |
| $MC_{85}L_{15}$-COOH | | | 1830/430-880 | 68[b3] | 1.38 |

[a]Determined by $^1$H NMR.
[b1]n-Hexane:Ethyl ether (4:1) insoluble part.
[b2]Celite filter.
[b3]n-Hexane:Ethyl ether (1:1) insoluble part.
[c]Measured by gel permeation chromatography (based on standard polystyrene).

An aqueous solution of the temperature-sensitive polyethylene glycol/polyester block copolymer according to the present invention maintains sol state having flowability at room temperature but forms a gel in a specific temperature range (20-60° C.). The temperature-sensitive behavior (sol-to-gel phase transition) of the block copolymer depending on the hydrophobicity of the introduced functional group can be measured using a viscometer. And, gelation property around the body temperature can be investigated by injecting the block copolymer into a mouse.

The temperature-sensitive behavior (sol-to-gel phase transition) of the block copolymer, onset temperature at which the temperature-sensitive behavior begins to occur and maximum viscosity at 37° C. are summarized in Table 2.

TABLE 2

| Polymer | Sol-to-gel phase-transition | Onset temperature (° C.) | Maximum viscosity (cP) |
|---|---|---|---|
| $MC_{97}L_3$-OBn | ○ | 42 | $17.5 \times 10^4$ |
| $MC_{97}L_3$-OH | ○ | 40 | $19.4 \times 10^4$ |
| $MC_{97}L_3$-COOH | ○ | 36 | $25.0 \times 10^4$ |
| $MC_{95}L_5$-OBn | ○ | 43 | $8.8 \times 10^4$ |
| $MC_{95}L_5$-OH | ○ | 38 | $12.5 \times 10^4$ |
| $MC_{95}L_5$-COOH | ○ | 34 | $15.6 \times 10^4$ |
| $MC_{93}L_7$-OBn | X | — | — |
| $MC_{93}L_7$-OH | ○ | 35 | $5.0 \times 10^4$ |
| $MC_{93}L_7$-COOH | ○ | 30 | $6.3 \times 10^4$ |
| $MC_{90}L_{10}$-OBn | X | — | — |
| $MC_{90}L_{10}$-OH | ○ | 32 | $5.0 \times 10^4$ |
| $MC_{90}L_{10}$-COOH | ○ | 25 | $5.6 \times 10^4$ |
| $MC_{87}L_{13}$-OBn | X | — | — |
| $MC_{87}L_{13}$-OH | X | — | — |
| $MC_{87}L_{13}$-COOH | ○ | 25 | $4.4 \times 10^4$ |
| $MC_{85}L_{15}$-OBn | X | — | — |
| $MC_{85}L_{15}$-OH | X | — | — |
| $MC_{85}L_{15}$-COOH | X | — | — |

The temperature-sensitive polyethylene glycol/polyester block copolymer according to the present invention not only allows the control of viscosity and biodegradation period, which is the advantage of the polyethylene glycol (PEG)- and polycaprolactone (PCL)-co-polylactide (PLLA)-based block copolymer, but also allows the control of temperature-sensitive behavior with the hydrophobicity of the bioactive functional group introduced at the side chain and is applicable to various tissue engineering applications and drug delivery systems. In addition, since an aqueous solution of the temperature-sensitive polyethylene glycol/polyester block copolymer according to the present invention having a bioactive functional group introduced into a side chain thereof exhibits sol-to-gel phase transition behavior at various temperature ranges depending on the composition of the hydrophobic moiety and the introduction of various functional groups such as hydroxyl, amine, carboxyl, etc., the block copolymer can be used as a biomaterial which forms gel not only at the human body temperature but also at temperatures slightly higher or lower than the body temperature. Also, the biodegradation period can be controlled.

For a temperature-sensitive block copolymer to be utilized for injectable drug delivery systems or supports for tissue engineering applications, it should exhibit low viscosity, fast gelation and low molecular weight to be easily cleared from human body. The copolymer according to the present invention, which includes caprolactone and lactide having various bioactive functional groups at a side chain thereof, allows the control of temperature-sensitive behavior with the hydrophobicity of the introduced functional groups and has a molecular weight close to the expected value. Also, since the copolymer according to the present invention can be made to have low viscosity and low molecular weight, which are necessary for biocompatibility and temperature sensitivity, it can stably load and release a drug by inducing interactions between the functional groups and the drug when prepared into drug delivery systems such as granule, hydrogel, etc. And, if the copolymer according to the present invention is used as a support for tissue engineering by introducing a peptide, it can improve adhesion and affinity to cells. Further, it can be used as an adhesion inhibitor which is implanted into a surgical site in the form of an injection after surgical operation to prevent adhesion between tissues for a predetermined period of time.

EXAMPLES

The present invention will be described in more detail through examples. The following examples are for illustrative purposes only and it will be apparent to those skilled in the art not that the scope of this invention is not limited by the examples.

Example 1

Preparation of Lactide Monomer [BMDD] Having Benzyl Ether Group Introduced into Side Chain (S)-2-Amino-3-benzyloxypropionic acid (20 g, 102.5 mmol) was dissolved in 0.7 M trifluoroacetic acid (TFA) aqueous solution (200 mL) and sodium nitrite ($NaNO_2$, 10.6 g, 153.7 mmol) dissolved in distilled water (100 mL) were added dropwise at room temperature for 3 hours with stirring using a dropping funnel. After further stirring for 4 hours, the mixture was washed with ethyl acetate (EA) and supersaturated sodium chloride aqueous solution (brine) using a separatory funnel and dried with magnesium sulfate (MgSO$_4$). After removing the solvent using a rotary evaporator, the product was dried under reduced pressure. The prepared compound was identified by $^1$H-NMR.

The prepared compound 3-benzyloxy-2-hydroxypropionic acid (16 g, 81.5 mmol) was dissolved in previously purified methylene chloride (MC, 190 mL) under high-purity nitrogen atmosphere and triethylamine (8.25 g, 81.5 mmol) was added. Then, a solution of 2-bromopropionyl bromide (17.6 g, 81.5 mmol) and 4-dimethylaminopyridine (DMAP, 1 g, 8.15 mmol) dissolved in methylene chloride (MC, 95 mL) was added dropwise at room temperature for 16 hours with stirring using a dropping funnel. The produced salt was removed by precipitating in ether (500 mL) and filtering. After removing the solvent using a rotary evaporator, the product was dried under reduced pressure. The prepared compound was identified by $^1$H-NMR.

The prepared compound 3-benzyloxy-2-(2-bromopropanoyloxy)propanoic acid (24 g, 72.5 mmol) was dissolved in acetone (300 mL) and reacted with excess potassium iodide (KI, 120 g, 725 mmol) at 65° C. for 12 hours. After the reaction was completed, the obtained dark-red oil was washed with ethyl acetate (EA) and 2 M sodium thiosulfate (Na$_2$S$_2$O$_3$) aqueous solution using a separatory funnel and dried with magnesium sulfate (MgSO$_4$). After removing the solvent using a rotary evaporator, the product was dried under reduced pressure. The prepared compound was identified by $^1$H-NMR.

Figure 1:
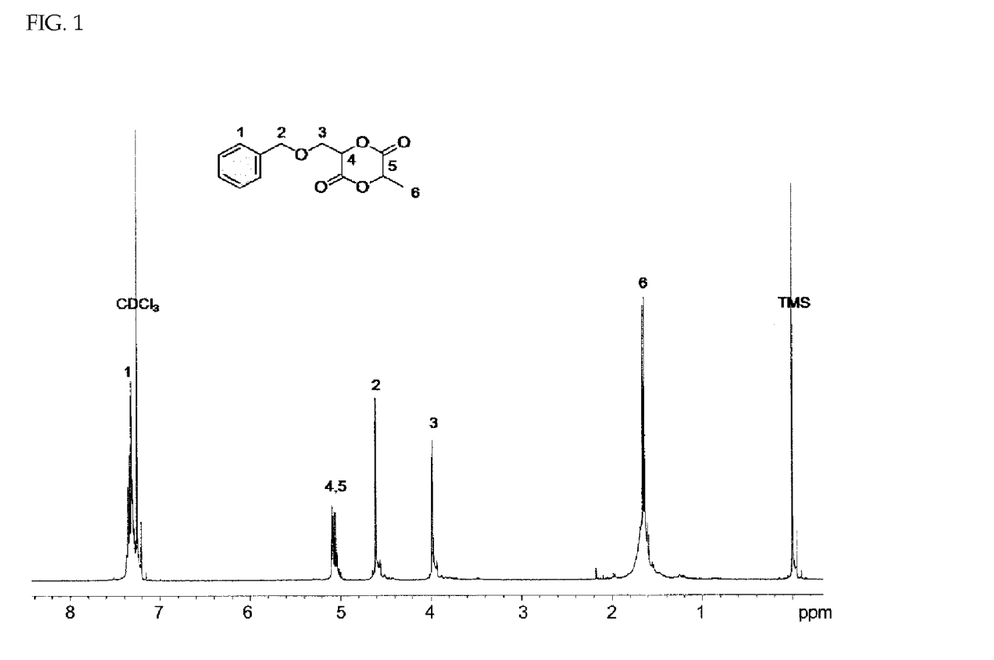
FIG. 1 shows a $^1$H-NMR spectrum of lactide having a benzyl ether group introduced into a side chain thereof.

The prepared compound 3-benzyloxymethyl-6-methyl-1,4-dioxane-2,5-dione (5.12 g, 11.9 mmol) was dissolved in methylene chloride (MC, 100 mL) under high-purity nitrogen atmosphere and N,N-diisopropylethylamine (DIEA, 4.6 mL, 27.7 mmol) dissolved in acetone (1000 mL) was added dropwise at 75° C. for 8 hours with stirring using a dropping funnel. After further stirring for 2 hours and removing the solvent using a rotary evaporator, the reaction solution was filtered through Celite. Then, the produced salt was removed through precipitation by adding ether (100 mL). The prepared compound was subjected to column chromatography using hexane:ethyl acetate (v/v, 3:1) as a mobile phase to remove oligomers. The product was subjected to column chromatography using hexane:ethyl acetate (80:20) as a mobile phase to separate isomers (R$_f$=0.25). The separated compound was recrystallized with ether to obtain a white crystalline solid. The prepared monomer 3-benzyloxymethyl-6-methyl-1,4-dioxane-2,5-dione (BMDD) was identified by $^1$H-NMR [FIG. 1].

Example 2

Preparation of methoxy polyethylene glycol-(polycaprolactone-co-polylactide Having Benzyl Ether Group Introduced into Side Chain) Block Copolymer [MPEG-PCL/PBMDD]

Figure 2:
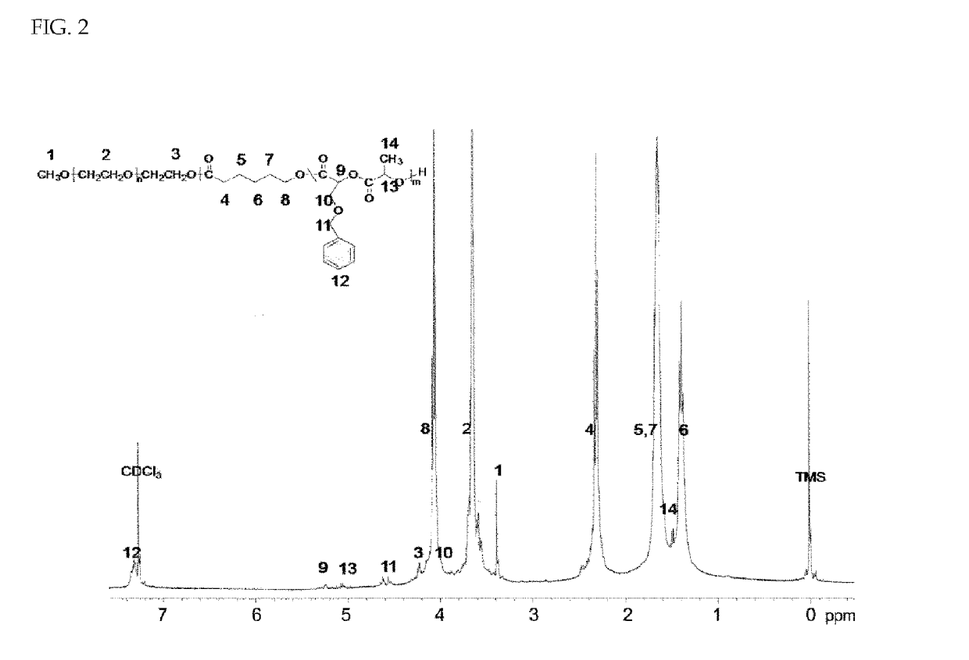
FIG. 2 shows a $^1$H-NMR spectrum of a polylactide (PBMDD) block copolymer having a benzyl ether group introduced into a methoxy polyethylene glycol (MPEG)-polycaprolactone (PCL)-co-side chain.

To synthesize an MPEG-PCL/PBMDD block copolymer having a molecular weight of 3150 g/mole, methoxy polyethylene glycol (MPEG, 1.51 g, 2.01 mmol) and toluene (80 mL) were put in a well-dried 100-mL round-bottom flask and azeotropic distillation was performed at 130° C. for 3 hours using a Dean-Stark trap. After removing the toluene with only 50 mL left and cooling to room temperature, previously purified caprolactone (CL, 4.34 g, 38 mmol) and benzyl ether lactide (BMDD, 0.5 g, 2 mmol) were added. Then, reaction was performed at 130° C. for 24 hours after adding Sn(Oct)$_2$ (3 mL) as a polymerization catalyst. All the procedures were conducted under high-purity nitrogen atmosphere. After the reaction, the reaction solution was precipitated by slowly dropping on a mixture of hexane (800 mL) and ether (200 mL) to remove unreacted monomers or initiator. The produced precipitate was dissolved in methylene chloride (MC) and filtered through filter paper. After removing the solvent using a rotary evaporator, the product was dried under reduced pressure. The molecular weight of the prepared copolymer was measured by $^1$H-NMR. It had a molecular weight of 3300 g/mole, similarly to a theoretically expected value. The copolymer was found to have a narrow polydispersity of 1.31 from GPC measurement [FIG. 2].

Example 3

Introduction of Hydroxyl Group into methoxy polyethylene glycol-(polycaprolactone-co-polylactide Having Benzyl Ether Group Introduced into Side Chain) Block Copolymer [MPEG-PCL/PBMDD-OH]

Figure 3:
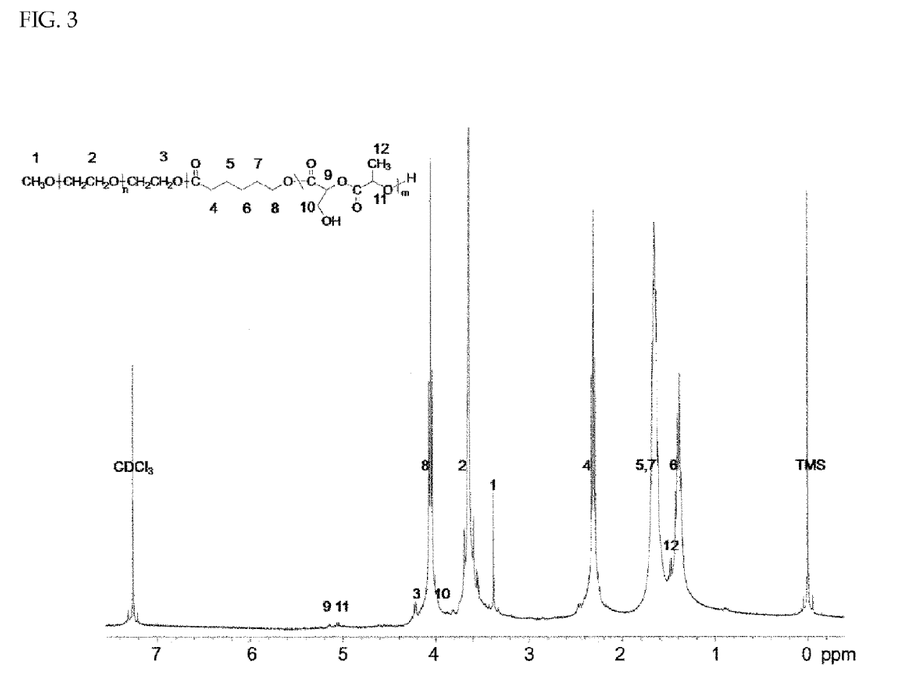
FIG. 3 shows a $^1$H-NMR spectrum of a block copolymer prepared in Example 2 having a hydroxyl group introduced through reduction.

The MPEG-PCL/PBMDD block copolymer (1 g) and palladium on carbon (Pd/C, 500 mg) were added to anhydrous tetrahydrofuran (THF, 100 mL). Reaction was performed at room temperature for 12 hours by stirring the mixture while supplying hydrogen bubbles using a syringe needle. After the reaction, the mixture was filtered through Celite. After removing the solvent using a rotary evaporator, the product was dried under reduced pressure. The introduction of a hydroxyl group into the side chain of the copolymer was identified by $^1$H-NMR from the disappearance of the benzyl peak at 7.3 ppm [FIG. 3].

Example 4

Introduction of Carboxyl Group into methoxy polyethylene glycol-(polycaprolactone-co-polylactide Having Hydroxyl Group Introduced into Side Chain) Block Copolymer [MPEG-PCL/PBMDD-COOH]

Figure 4:
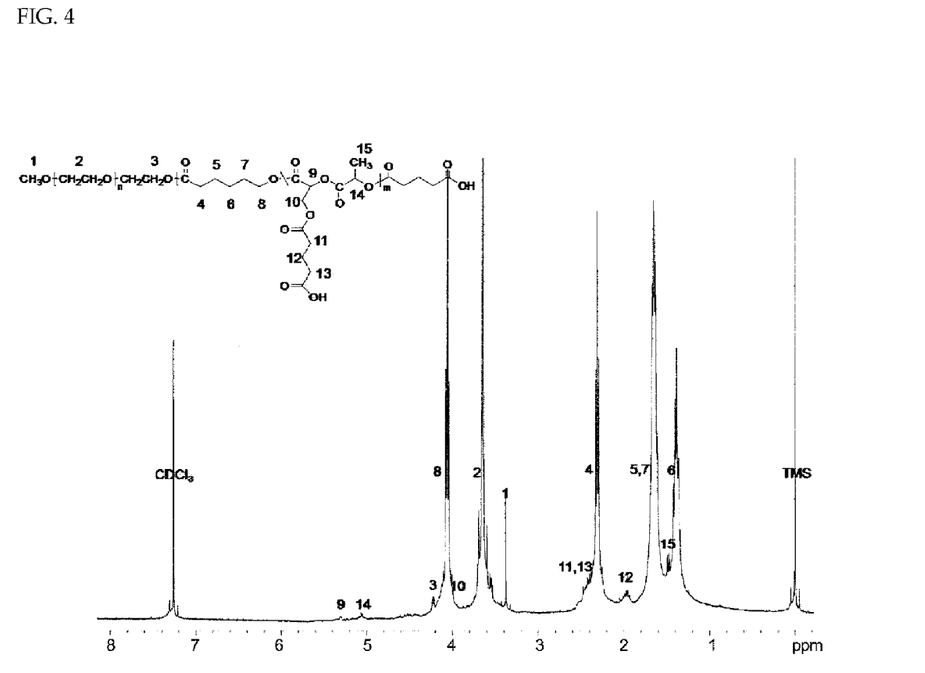
FIG. 4 shows a $^1$H-NMR spectrum of a block copolymer prepared in Example 3 having a carboxyl group introduced.

The MPEG-PCL/PBMDD-OH block copolymer (1 g) and toluene (80 mL) were put in a well-dried 100-mL round-bottom flask and azeotropic distillation was performed at 130° C. for 3 hours using a Dean-Stark trap. After removing the toluene with only 30 mL left and cooling to room temperature, glutaric anhydride (GA, 0.52 g) was added. Then, reaction was performed at 100° C. for 24 hours after adding acetic acid (0.6 mL) as a polymerization catalyst. All the procedures were conducted under high-purity nitrogen atmosphere. After the reaction, the reaction solution was precipitated by slowly dropping on a mixture of hexane (800 mL) and ether (200 mL) to remove unreacted monomers or initiator. The produced precipitate was dissolved in methylene chloride (MC) and filtered through filter paper. After removing the solvent using a rotary evaporator, the product was dried under reduced pressure. The molecular weight of the prepared copolymer was measured by $^1$H-NMR and a peak characteristic of the introduced carboxyl group was observed [FIG. 4].

Example 5

Introduction of Amine Group into methoxy polyethylene glycol-(polycaprolactone-co-polylactide Having Hydroxyl Group Introduced into Side Chain) Block Copolymer [MPEG-PCL/PBMDD-NH$_2$]

Figure 5:
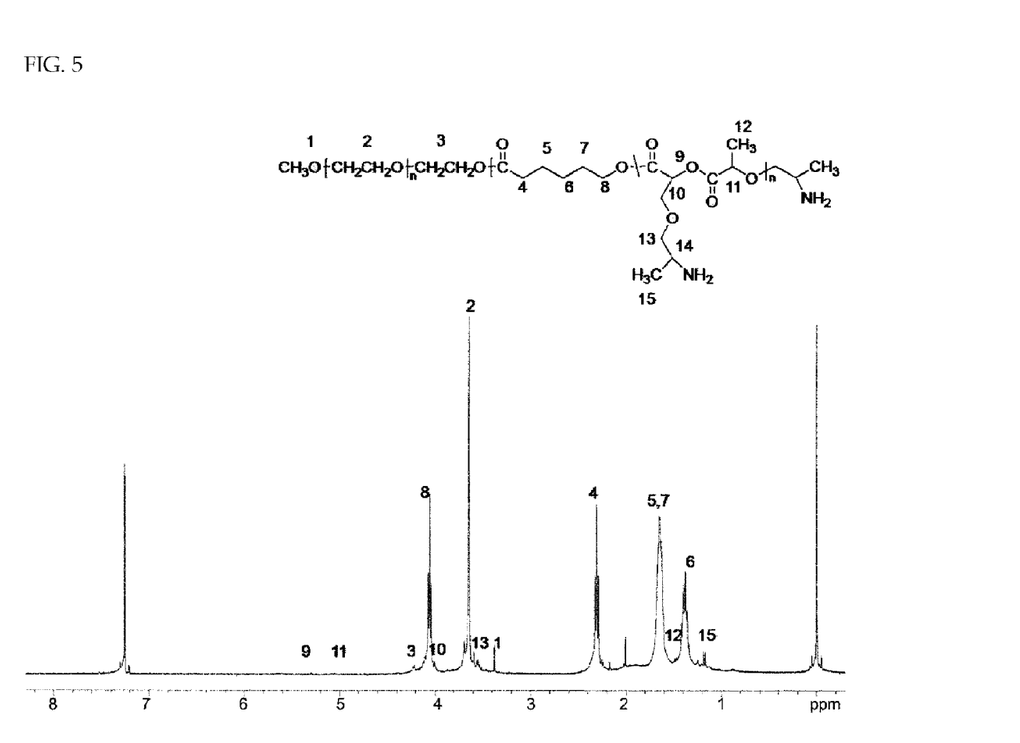
FIG. 5 shows a $^1$H-NMR spectrum of a block copolymer prepared in Example 3 having an amine group introduced.

The MPEG-PCL/PBMDD-OH block copolymer (1 g) and toluene (80 mL) were put in a well-dried 100-mL round-bottom flask and azeotropic distillation was performed at 130° C. for 3 hours using a Dean-Stark trap. After removing the toluene with only 30 mL left and cooling to room temperature, 2-methylaziridine (0.52 g) was added. Then, reaction was performed at 50° C. for 24 hours after adding acetic acid (0.6 mL) as a polymerization catalyst. All the procedures were conducted under high-purity nitrogen atmosphere. After the reaction, the reaction solution was precipitated by slowly dropping on a mixture of hexane (700 mL) and ether (300 mL) to remove unreacted monomers or initiator. The produced precipitate was dissolved in methylene chloride (MC) and filtered through filter paper. After removing the solvent using a rotary evaporator, the product was dried under reduced pressure. The molecular weight of the prepared copolymer was measured by $^1$H-NMR and a peak characteristic of the introduced amine group was observed [FIG. 5].

Example 6

Introduction of Peptide into methoxy polyethylene glycol-(polycaprolactone-co-polylactide Having Carboxyl Group Introduced into Side Chain) Block Copolymer [MPEG-PCL/PBMDD-RGD]

Figure 6:
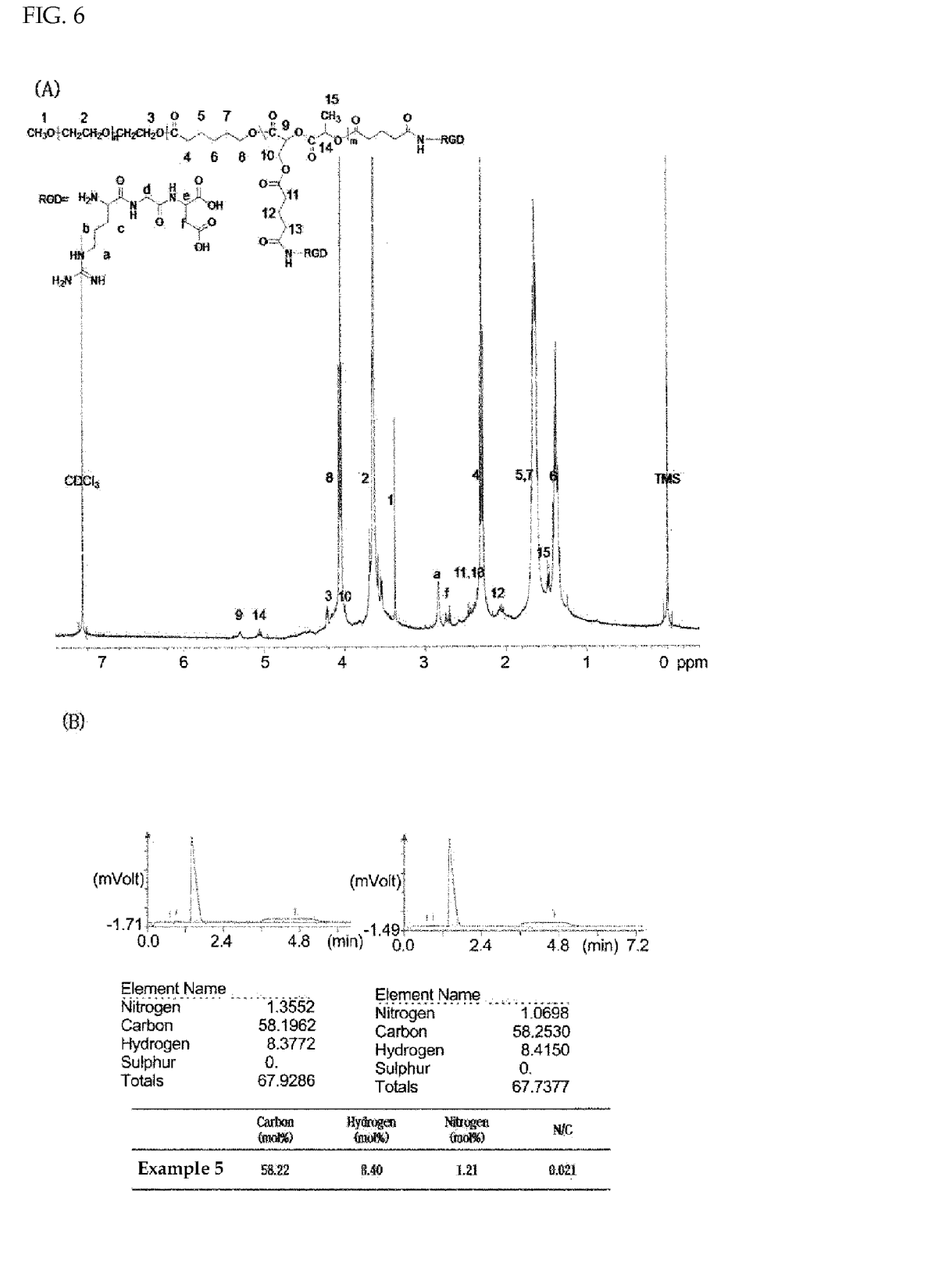
FIG. 6 shows a $^1$H-NMR spectrum (A) and an elemental analysis result (B) of a block copolymer prepared in Example 4 having a peptide introduced.

The MPEG-PCL/PBMDD-COOH block copolymer (1 g) was reacted at room temperature for 24 hours with N-hydroxysuccinimide (NHS, 1 g), N,N'-dicyclohexylcarbodiimide (DCC, 1.8 g) and 4-dimethylaminopyridine (DMAP, 0.007 g) dissolved in anhydrous dimethyl sulfoxide (DMSO, 3 mL). All the procedure was conducted under high-purity nitrogen atmosphere. After the reaction, the reaction solution was precipitated in excess ether and ultrasonically washed using methanol. After removing the solvent, the product was dried under reduced pressure. The prepared copolymer (0.1 g) and Arg-Gly-Asp (RGD, 20 mg) were dissolved in anhydrous dimethyl sulfoxide (DMSO, 5 mL) and reacted at room temperature for 4 days after adding triethylamine (0.25 mL). After the reaction, the resulting copolymer was precipitated in a mixture of hexane (100 mL) and ether (200 mL), dialyzed through a cellulose membrane for 2 days and then freeze-dried [FIG. 6].

Example 7

Figure 7:
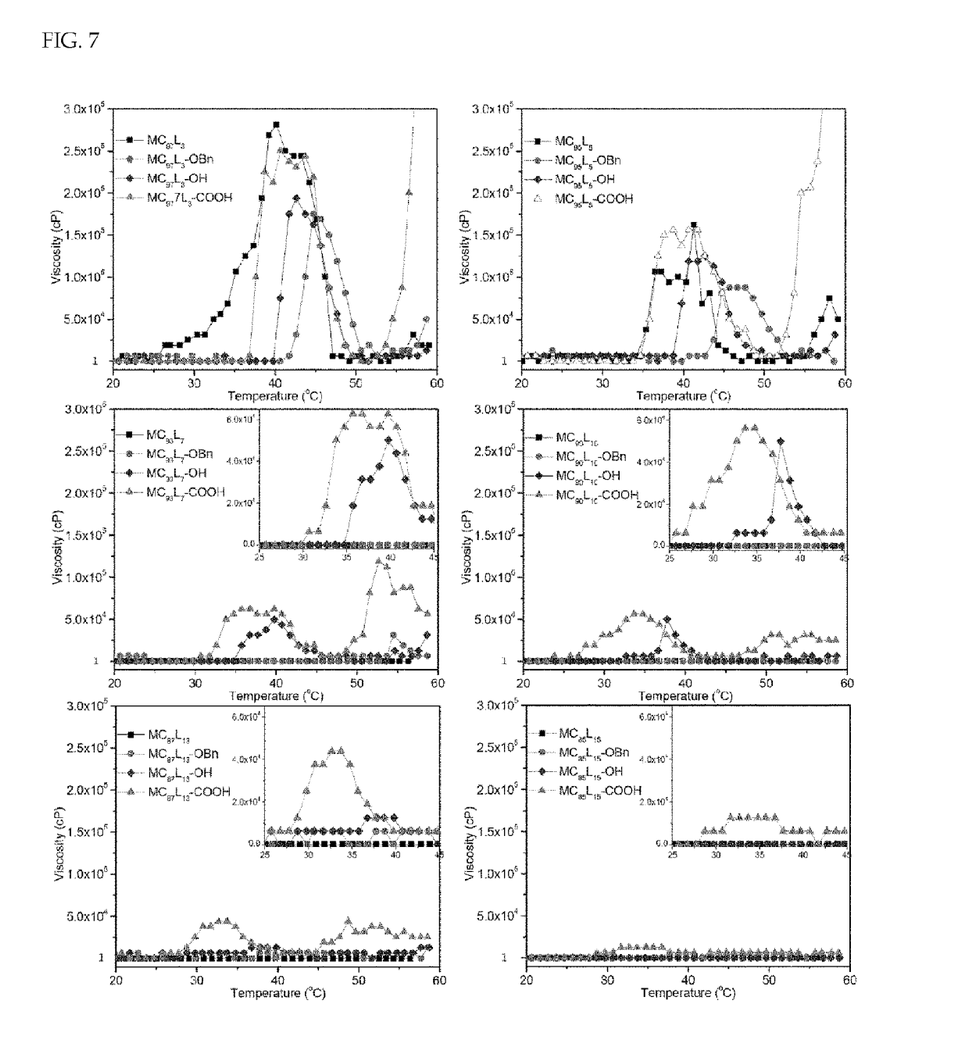
FIG. 7 shows a result of measuring the temperature-dependent phase transition behavior of block copolymers prepared in Example 2 and having different functional groups introduced in Examples 3 and 4.

Control of Sol-to-Gel Phase Transition Behavior of methoxy polyethylene glycol-(polycaprolactone-co-polylactide Having Functional Group Introduced into Side Chain) Block Copolymer In order to observe the temperature-dependent phase transition behavior of the methoxy polyethylene glycol-(polycaprolactone-co-polylactide) block copolymers having the functional groups into the side chains, each copolymer was dissolved in distilled water to a concentration of 20 wt % and kept in a refrigerator at 4° C. for a day to maintain a uniformly dispersed state. The sol-to-gel phase transition behavior of the prepared polymer solution was measured using a viscometer with a spin rate fixed at 0.2 rpm while raising temperature from 10° C. to 60° C. at a rate of 1° C. per 2 minutes. It was confirmed that the temperature range exhibiting the phase transition behavior could be controlled with the hydrophobicity of the functional group introduced into the side chain [FIG. 7].

Example 8

Figure 8:
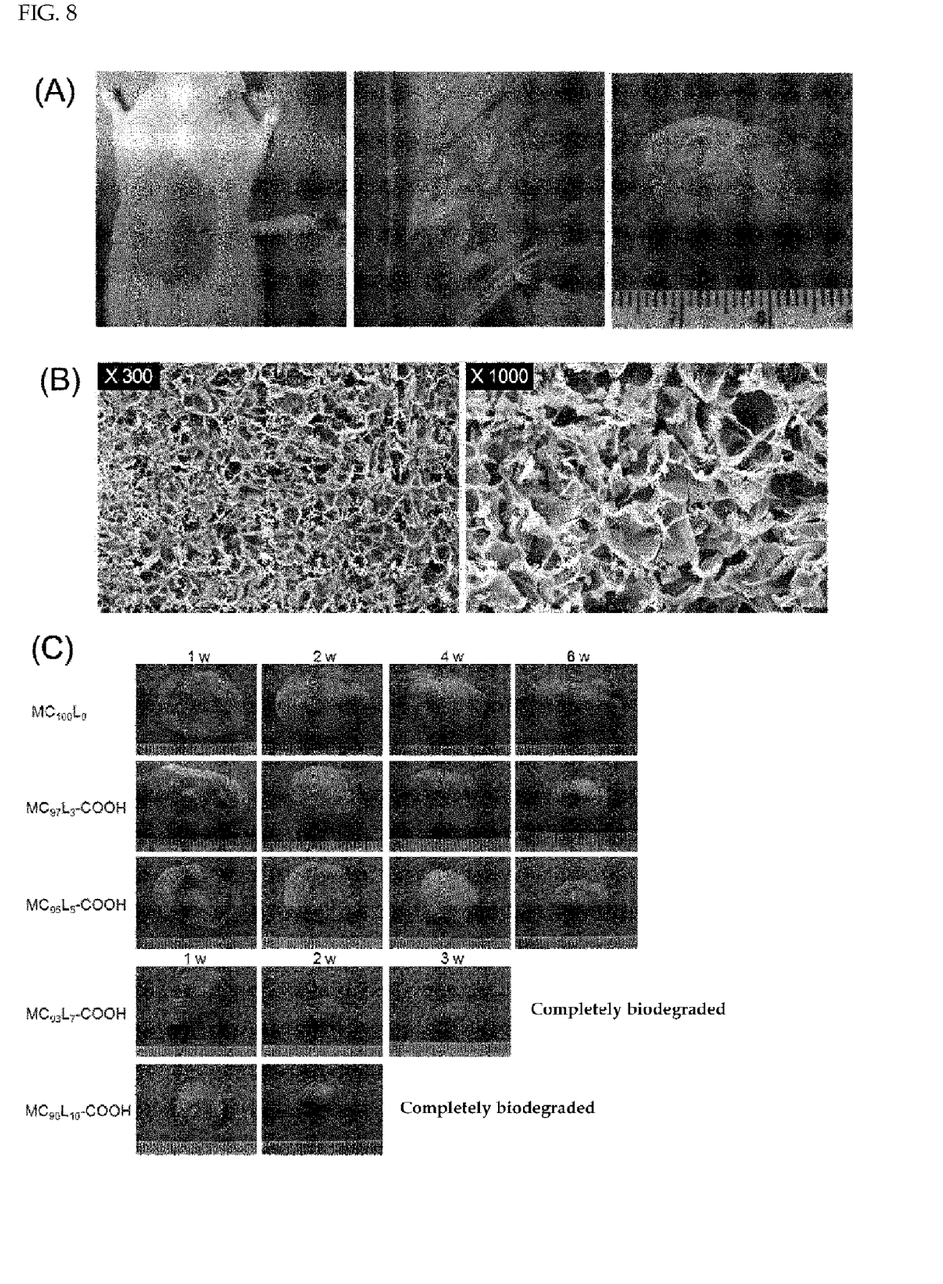
FIG. 8 shows (A) photographs confirming in vivo gelation, (B) cross-sectional SEM images and (C) photographs of a gel remaining after biodegradation of a block copolymer prepared in Example 4, obtained after subcutaneously injecting a solution of the block copolymer into a mouse.

In Vivo Gelation of methoxy polyethylene glycol-(polycaprolactone-co-polylactide Having Functional Group Introduced into Side Chain) Block Copolymer In order to confirm sol-to-gel phase transition around the body temperature, a solution of the methoxy polyethylene glycol-(polycaprolactone-co-polylactide) block copolymer having a carboxyl group introduced was maintained in sol phase at room temperature and 1 mL was subcutaneously injected into a mouse using a disposable syringe. 24 hours, it was observed whether gelation occurred by cutting the injection site open. It was observed that the solution of the methoxy polyethylene glycol-(polycaprolactone-co-polylactide) block copolymer having a carboxyl group introduced formed gel quickly in vivo and the block copolymer exhibited biodegradability with time. Also, the cross-sectional SEM image revealed that the block copolymer gel had a porous structure, suggesting that it is applicable to drug delivery systems and supports for tissue engineering [FIG. 8].

The temperature-sensitive polyethylene glycol/polyester block copolymers according to the present invention having various bioactive functional groups introduced into side chains thereof allow easy control of temperature-sensitive behavior and are applicable to temperature-sensitive injectable drug delivery systems since they can easily load and release drugs or bioactive agents in response to temperature change. Also, controlled drug release can be achieved by inducing interaction between the functional groups and the drugs.

Since the block copolymer is biodegradable and biocompatible, it can serve as a matrix that controls diffusion of a drug and can control the drug release behavior and speed as being hydrolyzed in human body.

If a peptide is introduced into the side chain, the block copolymer may be used as a support for tissue engineering that provides a space where cells can be attached and grow in culturing of cells and tissues in vivo and ex vivo.

Further, it can be used as an adhesion inhibitor which is implanted into a surgical site in the form of an injection after surgical operation to prevent adhesion between tissues for a predetermined period of time.

Accordingly, the temperature-sensitive polyethylene glycol/polyester block copolymer according to the present invention can be widely used as a drug delivery system, a support for tissue engineering or an adhesion inhibitor.

The present invention has been described in detail with reference to specific embodiments thereof. However, it will be appreciated by those skilled in the art that various changes and modifications may be made in these embodiments without departing from the principles and spirit of the invention, the scope of which is defined in the appended claims and their equivalents.

What is claimed is:
1. A temperature-sensitive polyethylene glycol/polyester block copolymer comprising:
 a hydrophilic moiety comprising polyethylene glycol; and
 a polyester-based hydrophobic moiety of Chemical Formula 1 comprising a caprolactone segment and a lactide segment having a bioactive functional group R introduced into a side chain thereof:

[Chemical Formula 1]

wherein x and y are mole fractions of the caprolactone segment and the lactide segment having the bioactive functional group R introduced, with x/y being from 0.01/99.99 to 99.99/0.01, and R is $-CH_2O-R_1-NH2$, $-CH_2O-R_1-NH-R_1-NH_2$, $-CH_2O-R_1-NH$-peptide, Arg-Gly-Asp, Gly-Pro-Glu, Arg-Gly-Asp-Ser, Gly-Gly-Ala, Gly-Arg-Gly-Asp-Ser, Gly-Arg-Gly-Asp-Thr-Pro, Gly-Arg-Gly-Asp-Ser-Pro, a protein comprising an amine structure or a polyamine having a molecular weight of 350-2,000 g/mole, and R has an amine group at the end of the molecular chain, wherein $R_1$ is $(C_1\text{-}C_{20})$ alkylene with or without carbonyl, $(C_2\text{-}C_{20})$ alkenylene with or without carbonyl or $(C_2\text{-}C_{20})$ alkynylene with or without carbonyl and $R_2$ is $(C_1\text{-}C_{20})$ alkyl with or without carbonyl, $(C_2\text{-}C_{20})$ alkenyl with or without carbonyl or $(C_2\text{-}C_{20})$ alkynyl with or without carbonyl.

2. The temperature-sensitive polyethylene glycol/polyester block copolymer according to claim 1, wherein the molar ratio x/y of the caprolactone segment and the lactide segment having the functional group R introduced is from 70/30 to 99/1.

3. The temperature-sensitive polyethylene glycol/polyester block copolymer according to claim 1, wherein the polyethylene glycol has a molecular weight of 350-2,000 grams per mole (g/mole).

4. The temperature-sensitive polyethylene glycol/polyester block copolymer according to claim 1, wherein the copolymer has a molecular weight of 2,000-6,000 g/mole.

5. The temperature-sensitive polyethylene glycol/polyester block copolymer according to claim 1, which is in sol phase at room temperature but in gel phase at 30-60 degrees Celsius (° C.).

6. A drug delivery system comprising the temperature-sensitive polyethylene glycol/polyester block copolymer according to claim 1.

7. A support for tissue engineering comprising the temperature-sensitive polyethylene glycol/polyester block copolymer according to claim 1.

8. An adhesion inhibitor comprising the temperature-sensitive polyethylene glycol/polyester block copolymer according to claim 1.

9. The temperature-sensitive polyethylene glycol/polyester block copolymer according to claim 3, wherein the polyethylene glycol has a molecular weight of 350-1,500 g/mole.

10. The temperature-sensitive polyethylene glycol/polyester block copolymer according to claim 4, wherein the copolymer has a molecular weight of 2,000-5,000 g/mole.

* * * * *